(12) United States Patent
Cewers

(10) Patent No.: US 8,161,970 B2
(45) Date of Patent: Apr. 24, 2012

(54) GAS FLOW CONTROL IN A VENTILATOR

(75) Inventor: Göran Cewers, Limhamn (SE)

(73) Assignee: RIC Investments, LLC, Wilmington, DE (US)

( * ) Notice: Subject to any disclaimer, the term of this patent is extended or adjusted under 35 U.S.C. 154(b) by 1217 days.

(21) Appl. No.: 11/574,368

(22) PCT Filed: Sep. 1, 2005

(86) PCT No.: PCT/EP2005/009438
§ 371 (c)(1), (2), (4) Date: Oct. 22, 2007

(87) PCT Pub. No.: WO2006/024532
PCT Pub. Date: Mar. 9, 2006

(65) Prior Publication Data
US 2008/0092891 A1    Apr. 24, 2008

(30) Foreign Application Priority Data
Sep. 3, 2004  (SE) ........................................ 0402120

(51) Int. Cl.
*A61M 11/00* (2006.01)
(52) U.S. Cl. .............. 128/204.21; 128/203.12
(58) Field of Classification Search ............. 128/203.12, 128/203.22, 204.23, 207.18, 204.26, 205.11, 128/206.11, 204.21
See application file for complete search history.

(56) References Cited

U.S. PATENT DOCUMENTS

| | | | |
|---|---|---|---|
| 5,265,594 A | 11/1993 | Olsson et al. | |
| 5,400,777 A | 3/1995 | Olsson et al. | |
| 5,492,115 A * | 2/1996 | Abramov et al. | 128/205.24 |
| 6,089,229 A * | 7/2000 | Bathe et al. | 128/204.21 |
| 6,425,395 B1 | 7/2002 | Brewer et al. | |
| 7,201,166 B2 * | 4/2007 | Blaise et al. | 128/203.12 |
| 7,523,752 B2 * | 4/2009 | Montgomery et al. | 128/204.21 |

FOREIGN PATENT DOCUMENTS

| | | |
|---|---|---|
| DE | 10021782 | 11/2000 |
| EP | 0982043 | 3/2000 |
| EP | 1166813 | 1/2002 |
| WO | WO 00/45883 | 8/2000 |

* cited by examiner

*Primary Examiner* — Steven Douglas

(57) ABSTRACT

A system that provides a flow of gas to an airway of a user that includes a source of gas, a conduit that carries the flow of gas to the airway of a patient, a first valve that controls a pressure, flow, or volume, of the flow of gas, a pressure sensor coupled to the conduit between the valve and the patient that monitors a pressure of the gas in the conduit, and a controller that controls the valve based on an output of the pressure sensor. A restrictor is provided in the conduit between the pressure sensor and the patient that divides the fluid delivery system with a first smaller volume in the conduit between the valve and the restrictor and a second larger volume between the patient and the restrictor. The system controls the pressure, flow, or volume relative to the first volume.

20 Claims, 7 Drawing Sheets

GAS FLOW CONTROL IN A VENTILATOR

PRIORITY CLAIM

This application claims priority from Swedish Patent Application Ser. No. 0402120-0 filed Sep. 3, 2004.

TECHNICAL FIELD

The present invention pertains to a ventilator adapted to deliver a flow of gas to an airway of a user, and, in particular, to a ventilator with improved pressure control during inspiration.

BACKGROUND OF THE INVENTION

It is well known to utilize a ventilator, anesthesia machine, or pressure support device to deliver a fluid, such as oxygen, air, or other breathing gas or gas mixture, to an airway of patient to augment, supplement, or substitute the patient's own ventilatory effort and/or to treat the patient with a pressure support therapy. Of importance in such situations is the ability to accurately regulate or control the pressure, flow, and/or volume of gas delivered to the patient during the inspiratory phase of the respiratory cycle. For present purposes, the term "ventilator" is used to describe any system or device that delivers a flow of gas or pressurized gas to the airway of a user.

FIG. 1 illustrates the inspiratory components of a conventional ventilator. These components include a source of a first gas 30, such as air, and a source of a second gas 32, such as oxygen. The source of first gas typically includes a pressurized storage tank, blower, bellows, impeller, fan, piston, pressure generator, or the like, that provides pressured air at a pressure above ambient pressure. The source of oxygen is typically a pressurized oxygen storage tank, a central wall supply (typically found in a hospital), or an oxygen concentrator. In short, the sources of the first and second gas can be pressure generators that operate under the control of the ventilator, an independent gas supply, such as that available through a hospital's central gas delivery system, or a combination thereof.

In the embodiment of FIG. 1, a first valve 34 controls the mixing of the first gas and the second gas, and a second valve 36 control the pressure and/or flow of the gas mixture provided to the patient, as indicated by arrow A. Valves 34 and 36 are typically proportional valves, which are commercially available in a number of different variants. Such valves usually comprise an electromagnet, a membrane that usually is made of rubber, and a valve seat. The amount or percentage that the valve is opened is determined by the current flowing through the electromagnet. The resulting gas flow is approximately proportional to the current.

An alternative conventional inspiratory portion of a ventilator is shown in FIG. 2. In this embodiment, separate valves 38 and 40 control the supply of gas to the first gas (e.g., air) and the supply of the second gas (e.g., oxygen). The separate gas supplies are mixed downstream of the valves, typically using a mixing element or accumulator, for subsequent delivery to the patient. In each embodiment, the combined gas flow is carried by a primary conduit 42 to an external coupling provided on the ventilator housing. A flexible hose or patient circuit (not shown) couples to the external coupling an airway of the patient.

A conventional ventilator typically includes a flow sensor 44 and a pressure sensor 46 to measure the flow and pressure, respectively, of the gas delivered to the patient via the patient circuit. The output of flow sensor 44 and pressure sensor 46 is provided to a controller 50, which, in some ventilation modes, uses this information to control the flow, volume, and/or pressure of gas delivered to the patient. For example, the processor uses this information to control the actuation of valves 34, 36, 38, or 40 so that the desired flow, pressure, or volume of gas is administered to the patient.

In order to control the flow, volume, or pressure of gas delivered to the patient, the flow sensor and/or pressure sensors are used in a "closed loop" or feedback configuration. That is, the signals output by these sensors are provided to controller 50, which uses them to compare the actual flow, pressure, or volume, as determined from the sensors, with a set or desired quantity. The controller then controls the valves to reduce the error between the measured and the desired values. A typically controller 50 includes a PI or PID controller for comparing the measured values to the desired values and controlling the valves based thereon. An example of conventional ventilators that use such control techniques to provide pressure or volume control are described in U.S. Pat. Nos. 5,400,777 and 5,265,594. One disadvantage of conventional pressure/flow/volume control techniques, which is discussed in greater detail below, is that it is difficult for provide a control system that can quickly and accurately regulate the pressure, flow, or volume of gas using such techniques with a high level of stability.

DISCLOSURE OF THE INVENTION

Accordingly, it is an object of the present invention to provide a ventilator that overcomes the shortcomings of conventional ventilators. This object is achieved according to one embodiment of the present invention by providing a ventilator that includes a source of gas, a conduit that carries the flow of gas to the airway of a patient, a first valve that controls a pressure, flow, or volume, of the flow of gas, a pressure sensor operatively coupled to the conduit between the valve and the patient and adapted to monitor a pressure of the flow of gas in the conduit, and a controller adapted to control the valve based on an output of the pressure sensor. The ventilator further includes a restrictor provided in the conduit between the pressure sensor and the patient. The restrictor, in essence, divides the fluid delivery system such that a first volume is defined in the conduit between the valve and the restrictor, and a second volume is defined in the conduit between the patient and the restrictor and which includes the volume of the patient, wherein the first volume is less than the second volume. The control system controls the pressure, flow, or volume relative to the first volume so that an accurate, fast, and stable control of the pressure, flow, or volume is achieved These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BEST MODES FOR CARRYING OUT THE INVENTION

Figure 3:
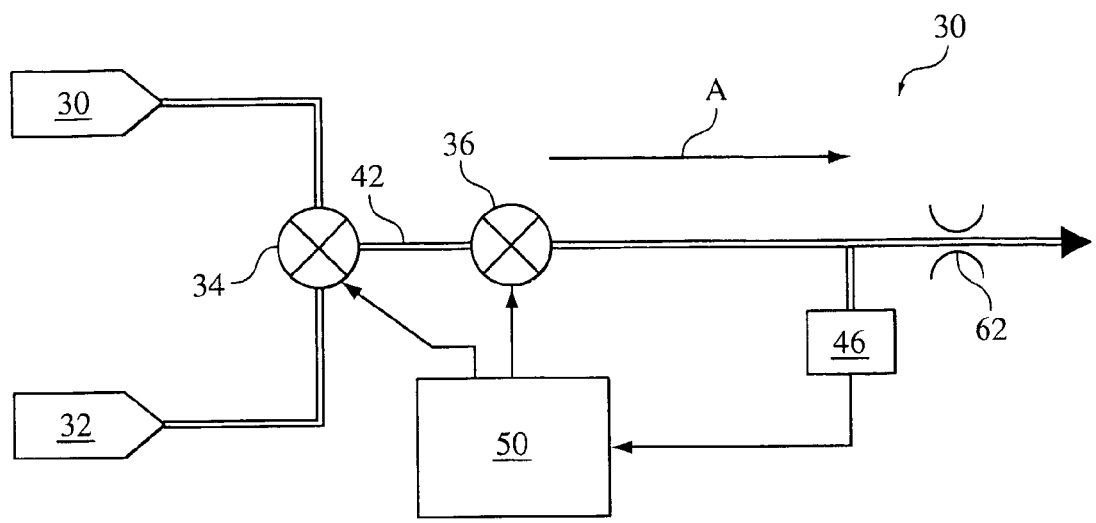
FIG. 3 is a schematic diagram of a first embodiment of a ventilator according to the principles of the present invention.

FIG. 3 is a schematic diagram of a first embodiment of a ventilator 60 according to the principles of the present invention. It should be noted that FIG. 3 illustrates only those components of the ventilator associated with the delivery of a flow of gas to a patient during the inspiratory phase of the respiratory cycle. The expiratory components are omitted. It should be further understood that the present invention contemplates that ventilator 60 can be a pressure support system, such as a CPAP or bi-level system. Such systems are a single limb systems. Instead of an expiratory limb, an exhaust vent is provided at or near the patient in the inspiratory limb. Such systems do not include expiratory related components.

Figure 1:
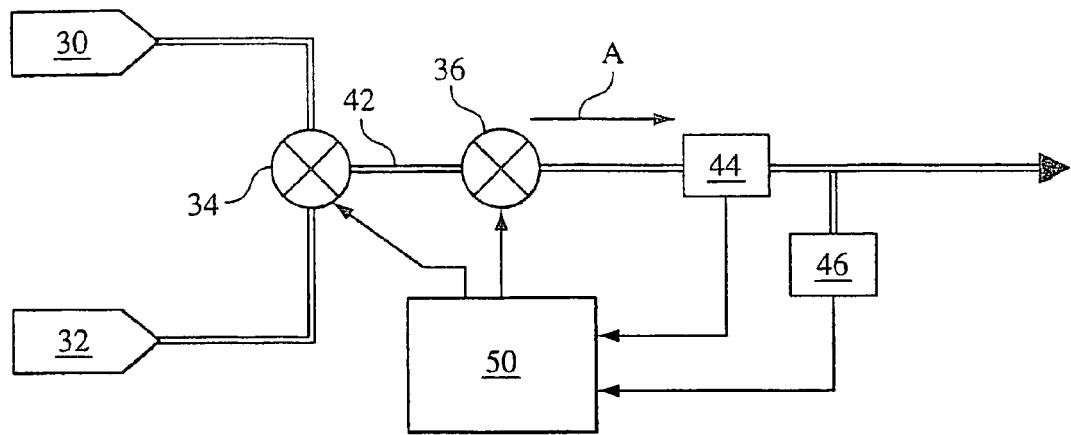
FIGS. 1 and 2 are schematic diagrams of two examples of conventional ventilators.

It can be appreciated from reviewing FIGS. 1 and 3, that the ventilator of the present invention is similar in many respects to a conventional ventilator. The main difference is the ventilator 60 includes a flow restrictor 62 provided in conduit 42 downstream of pressure/flow control valve 36. Thus, a source of a first gas 30 includes a pressurized storage tank, blower, bellows, impeller, fan, piston, pressure generator, compressors or any device that is capable of delivering gas at a pressure above ambient pressure. The source of first gas can be integral with the ventilator, i.e., disposed in the ventilator housing, which is typical if the source of first gas is a bellows, piston, compressor, blower, or the like. The present invention also contemplates that the source of first gas can be external to the ventilator, which is typical if the source of the first gas is a wall supply in a hospital. If the source of the first gas is external to the ventilator, input couples are provided on the ventilator that communicate the flow of gas to the ventilator. The source of second gas 32, such as oxygen, is typically a pressurized oxygen storage tank, a wall supply, or an oxygen concentrator, or any device capable of providing a supplemental gas.

The present invention contemplates that the ventilator of the present invention can include devices, components, software, communication links, etc., typically associated with ventilators. Examples of devices typically used with a ventilator include humidifiers, nebulizers, filters, etc. Although not shown, a user interface device can be provided to allow a user to manually set up and/or control the ventilator. This interface can be provided directly on the ventilator in the form of a keypad, touchscreen, knob, dials, etc., or it can be remote therefrom with a hardwired or wireless communication link being used to communicate the remote device with the ventilator to set up and/or control the ventilator.

Figure 5:
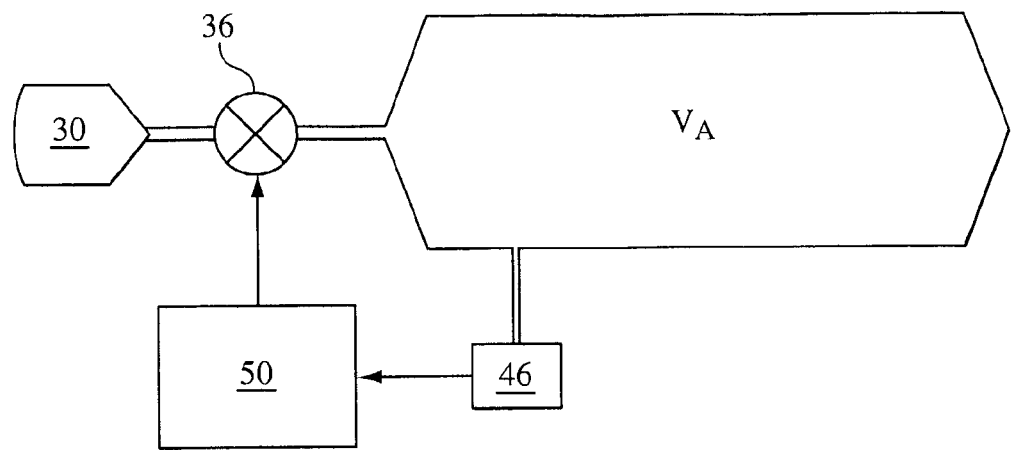
FIG. 5 is a schematic diagram illustrating the control system in a conventional ventilator.

In order to perhaps best understand the function of restrictor 62, the pressure/volume/flow control used in a conventional ventilation system must first be explained. As shown in FIG. 5, downstream of pressure/flow control valve 36 there exists a relatively large physical volume, which is represented by volume $V_A$. This volume includes the volume within the conduits that are internal to the ventilator, the flexible patient circuit coupled to the external coupling on the ventilator, the patient interface device that communicated the patient circuit with the patient's airway, the airways of the patient, which including the mouth, upper airway, trachea, and lungs. In a conventional ventilator, this relatively large volume is monitored by pressure sensor 46. The control system, which includes controller 50 and valve 36 attempts to control the system accurately based on this monitored parameter. For example, if the patient it to receive a flow of gas at a target pressure of 10 cmH$_2$O, the pressure sensor will measure the actual pressure and the controller will adjust the valve in an attempt to deliver the flow of gas at that target pressure.

However, effective pressure regulation is difficult in this type of arrangement due to the fact that the control system is attempting to regulate a relatively large volume that has inherent instability. For example, the ability to control the pressure deteriorates as a due to the transit time that it takes for a pressure change to effect a large volume of fluid: the greater the volume of fluid, the longer the transmit time. In other words, the large the volume of fluid being controlled by the control system, the slower the system responds to pressure changes. In addition, the patient circuit (tubes) and the patient himself or herself have internal resistances and volumes that affect the ability of a pressure change induced by the valve to take effect in the whole system. The tubes and the patient's respiratory system also include a certain amount of inherent flexibility, which is referred to as elastance, so that pressure changes cause the volume to expand or contract, thereby changing the volume on the control system. It can be appreciated that changes in the volume as the pressure is increased or decreased by the controller make it harder for the control system to accurately control that volume to a certain pressure level. In addition, the fluid itself is compressible. This effectively results in low pass filtering of the pressure generation between the valve and the pressure transducer. Thus, the control system has difficulty taking the measurements for pressure transducer 46 and using these signal to accurately and quickly control the pressure in a stable manner.

Figure 6:
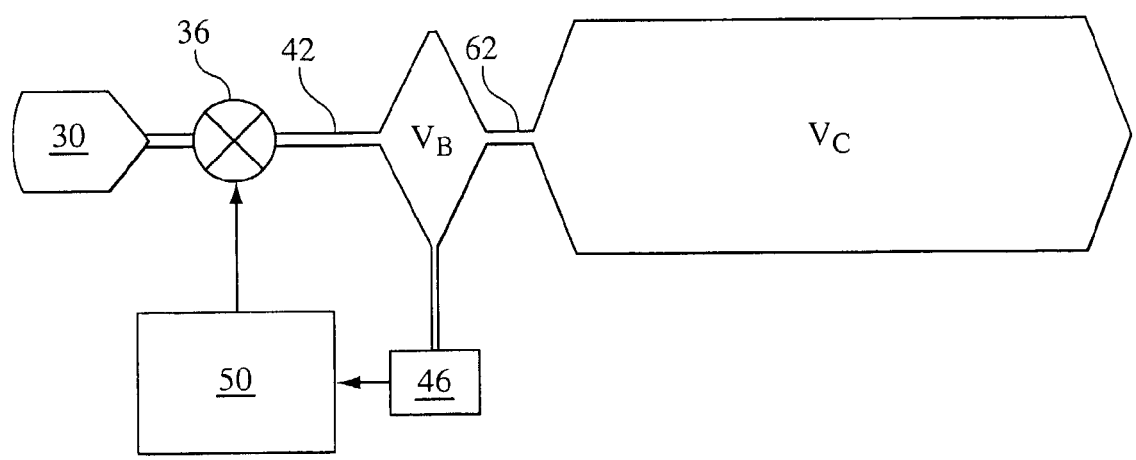
FIG. 6 is a schematic diagram illustrating the control system in a ventilator according to the principles of the present invention.

Restrictor 62, in essence, separates volume $V_A$ into two smaller volumes $V_B$ and $V_C$, as illustrated in FIG. 6. Pressure sensor 46 is arranged so as to measure the pressure of the smaller and closer to the valve 36 volume $V_B$, and the control system (including controller 50 and valve 36) is arranged to control the pressure of smaller volume $V_B$. In an exemplary embodiment of the present invention, volume $V_C$ is at least two times that of $V_B$. However, the present invention contemplates that volume $V_C$ can be ten times that of $V_B$ or more. The control system controls the pressure of volume $V_B$. Because this is a relatively small volume, with less inherent instability, e.g., less resistance to flow, less internal elastance, less gas mass to accelerate, and a relatively small volume of fluid contained therein, the control system is better able to accurately and quickly control the pressure of volume $V_B$, and in a much more stable fashion, than that of volume $V_A$. Thus, restrictor 62 partly isolates the pressure control loop from the large volumes to make it easier for the control system to control the pressure of the smaller volume accurately.

There is a fluid communication between volumes $V_B$ and $V_C$ through the restrictor. Thus, pressure control that is done with respect to volume $V_B$ is translated into volume $V_C$, albeit with a slight lag or delay. However, those skilled in the are can appreciated that the size of the restriction can be selected so as to minimize this delay will still providing a useful amount of separation between volumes $V_B$ and $V_C$ so that the control system functions with the desired degree of precision. It should also be noted that restrictor 62 is also configured such that the gas flow through the restriction is sufficient to provide an adequate ventilation of the patient with a certain pre-determined gas volume, e.g., a maximum minute volume. In an exemplary embodiment of the present invention, the flow restriction created by restrictor 62 is at least two times greater than a resistance along the conduit from valve 36 to the patient.

It should be further noted that providing an intentional restriction in the gas flow downstream of the pressure/flow controlling valves is counterintuitive to the proper function of a conventional ventilator. Using conventional wisdom, the flow of gas existing the valve is provided to the patient with as little resistance as possible so that there only is a minimal amount of pressure drop between the pressure controller (the valve) and the patient. Flow restrictions downstream of the valves in a conventional ventilator adversely affect their ability to properly deliver a flow of gas to the patient.

In an exemplary embodiment of the present invention, restrictor 62 is configured to have a pre-determined pressure-flow curve. This curve may have any one of a variety of configurations, for example linear or non-linear. A variety of configurations for restrictor 62 are contemplated by the present invention to provide the desired pressure-flow curve. For example, the restrictor may take the form of a fixed element, such as a net, mesh, screen, aerodynamically shaped element or elements, disposed in the flow path of conduit 42. The restrictor may also include one or more movable elements, such as flaps, slats, vanes, that alter the opening or geometry of the restrictor with changes in the pressure or flow to which the restrictor is subject. The present invention further contemplates that restrictor 62 can be removably disposed in conduit 42 so that different sizes, shapes, or configurations of restrictors can be chosen for different patient categories. This also allows for ease of cleaning of the restrictor. Moreover, the restrictor can be configured so as to have an adjustable flow restriction, so that the degree of flow restriction can be controlled either manually or automatically. For example the present invention contemplates that controller 50 may adjust the amount restriction provided by restrictor based on the monitored conditions of the system and/or patient, so that a suitable degree of restriction is provided that strikes a balance between the objectives noted above are achieved.

In a further exemplary embodiment, the restriction provided by restrictor 62 is variable so that the amount of fluid communication between volumes $V_B$ and $V_C$ can be dynamically adjusted, e.g., for low minute volumes, the restriction is adjusted to a maximum value, so that the control of the pressure in volume $V_C$ is as fast as possible. This is particularly advantageous in the ventilation of children or neonates, in which case it should be possible to control small minute volumes with high accuracy and with quickness of the pressure control. Likewise, where large minute volumes are needed, the restriction may also be released, such that still a restriction is present, but in such a way that higher instantaneous flows may be generated by the inspiratory portion of the ventilator. As noted above the variable choking function of the restrictor may be implemented in different ways, e.g., elements such as nets or aerodynamically shaped elements, can be moveably inserted into the flow channel.

In the embodiment illustrated in FIG. 3, volume $V_B$ corresponds to the volume of the tubes, conduits, and other pneumatic components between valve 34 and restrictor 62. The present invention also contemplates providing an additional volume, for example, a chamber coupled to conduit 42 between valve 34 and restrictor 62, so that volume $V_B$ is sufficient for pressure control purposes.

The present invention also contemplates that volume $V_B$ can be a variable volume. For example, a piston, collapsible tube, or any other mechanism for selectively changing a volume, can be coupled to volume $V_B$ (e.g., by coupling the adjustable volume to conduit 42 between valve 34 and restrictor 62, so that volume $V_B$ is adjustable and, hence, controllable. This is useful, for example, in situations where it is desirable to maintain a certain ratio between volume $V_B$ and volume $V_C$.

Figure 2:
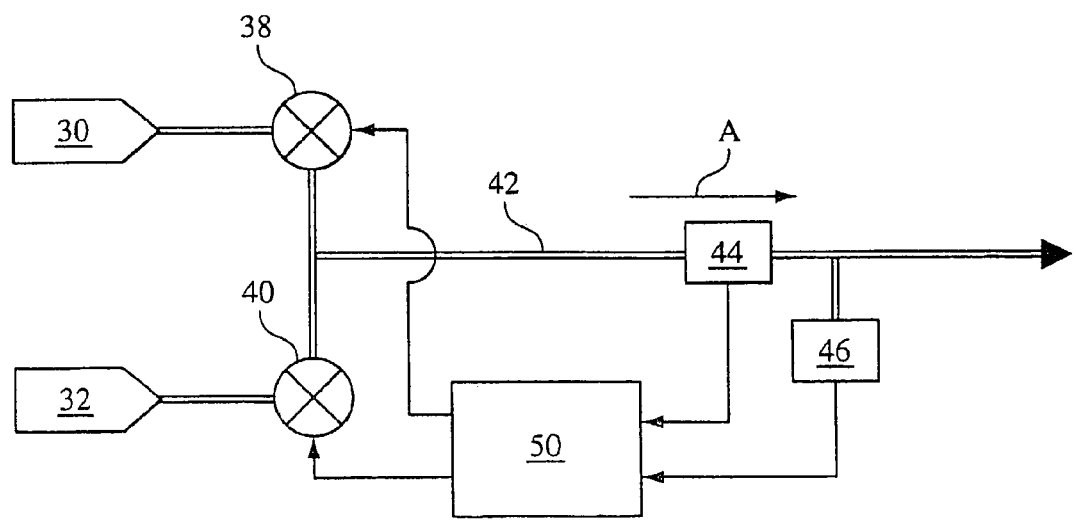
Figure 4:
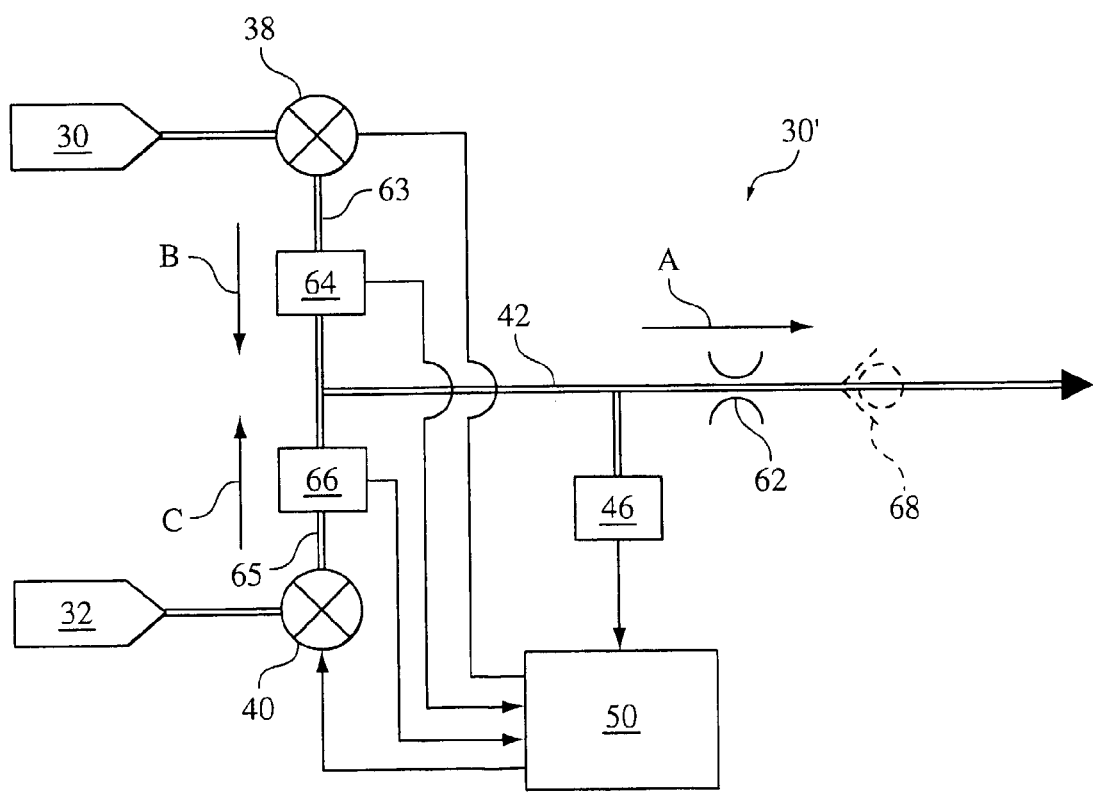
FIG. 4 is a schematic diagram of a second embodiment of a ventilator according to the principles of the present invention.

A second embodiment of a ventilator 30' according to the principles of the present invention is schematically illustrated in FIG. 4. In the embodiment, like that of the conventional ventilator shown in FIG. 2, two valves 38 and 40 are provided to control the flow of a first gas from first source 30 via gas flow path 63 and a second gas from second source 32 via gas flow path 65. The two gas flows, which are illustrated by arrows B and C are combined to define gas flow A for delivery to the user. In this embodiment, flow sensors 64 and 66 are disposed in the gas flow paths to monitor the direction and/or rate of flow of each gas prior to being mixed. Restrictor 62, as discussed above, is provided downstream of valves 64 and 66, and a pressure sensor is coupled to the gas flow path between valves 64 and 66 and restrictor 62.

Although not illustrated in this figure, the present invention contemplates that other sensors can be provided in the ventilatory system and used on fine-tune the control the system. For example, pressure sensors can be provided along the patient circuit to monitor the pressure at a location along the circuit. This is helpful in order to characterize dynamical pressure drops and in order to compensate the pressure regulator for the purpose of achieving a more accurate pressure regulation. The present invention, also contemplates providing a pressure sensor at, near, or in the patient's airway to provide an accurate measure of the actual pressure experienced by the patient. Again, this pressure can be used to provide even better control of the pressure control system.

The present invention also contemplates providing an optional on-way check valve 68 downstream of restrictor 62. Check valve 68 is configured to allow a flow gas A to the patient, but prevent a flow of gas in an opposite direction. This prevents or minimizes pressure/flow oscillations that are generated downstream of the check valve from influencing the control system upstream of the check valve.

The present invention contemplates that flow sensors 64 and 66 are any sensor suitable for use in measuring or merely monitoring the flow of gas passing through conduits. A common technique for measuring flow is to use a flow restrictor in form of a tube package or a fine-meshed net to create a pressure drop along a gas flow path. A differential pressure transducer measures the pressure drop across the flow restrictor. The signal output from the differential pressure sensor is a measure for the flow in the gas flow path. A tube package possesses good flow linearity (pressure vs. flow), but requires a rather large volume. A fine-meshed net has a poorer linearity, but constitutes itself a small volume. In order to obtain a good linearity over a large flow range, a relatively large net surface is necessitated. If the net is lying as a cross section through a circular channel, this will add to a large volume, if a good linearity is desired.

Figure 7:
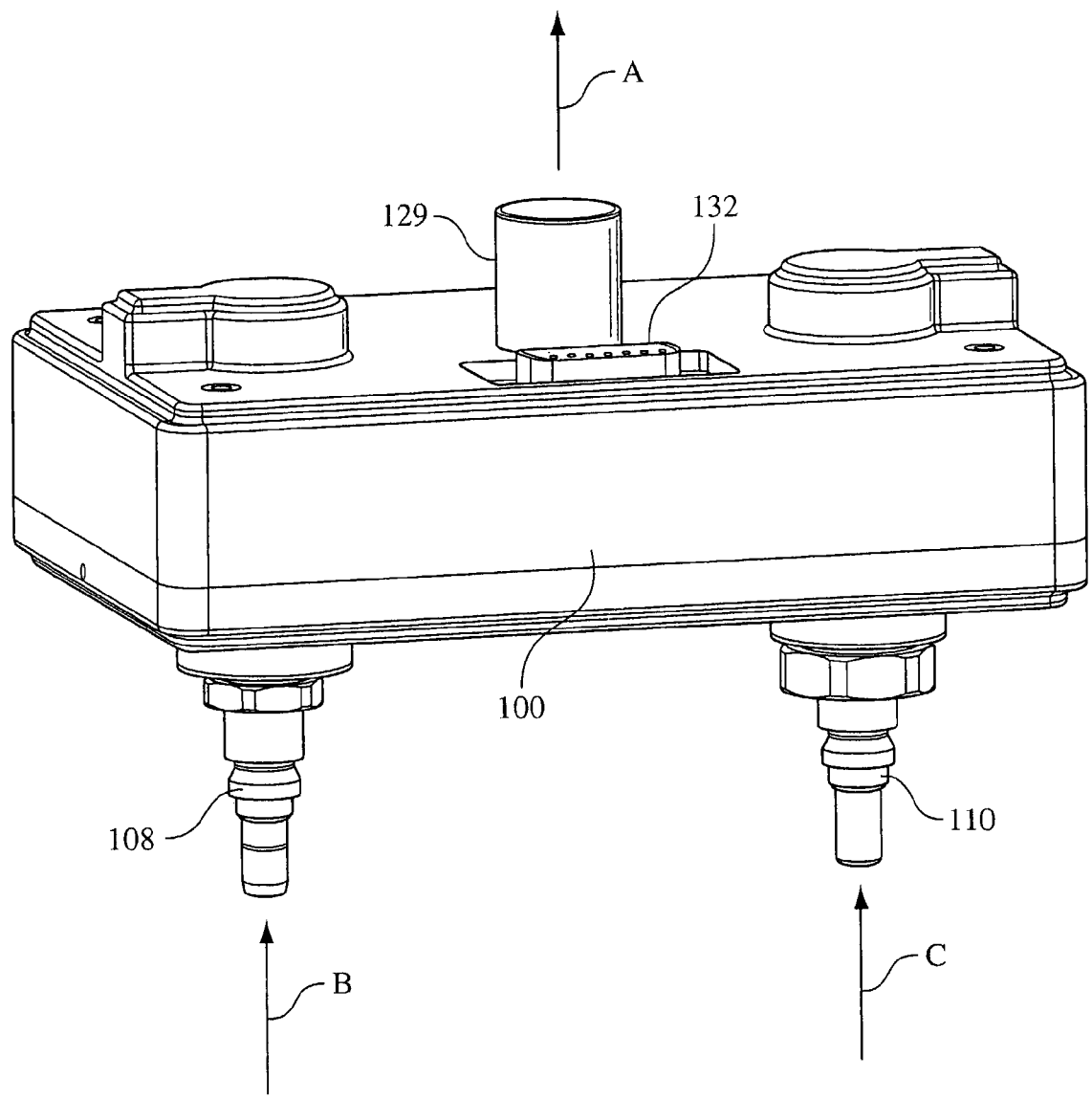
FIG. 7 is a perspective view of a valve assembly for use in the ventilator of FIG. 4.
Figure 8:
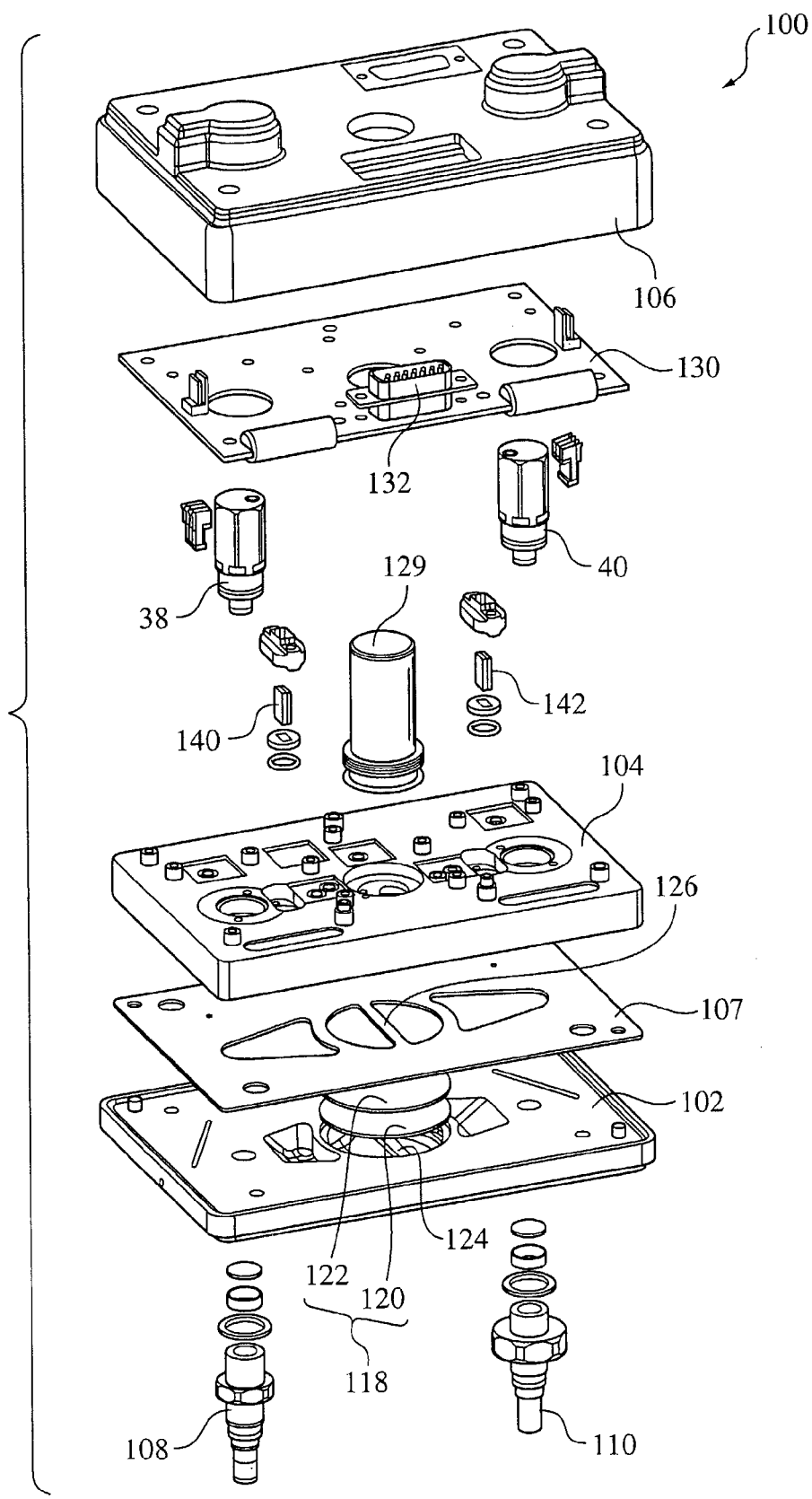
FIG. 8 is an exploded view of the valve assembly of FIG. 7.
Figure 9:
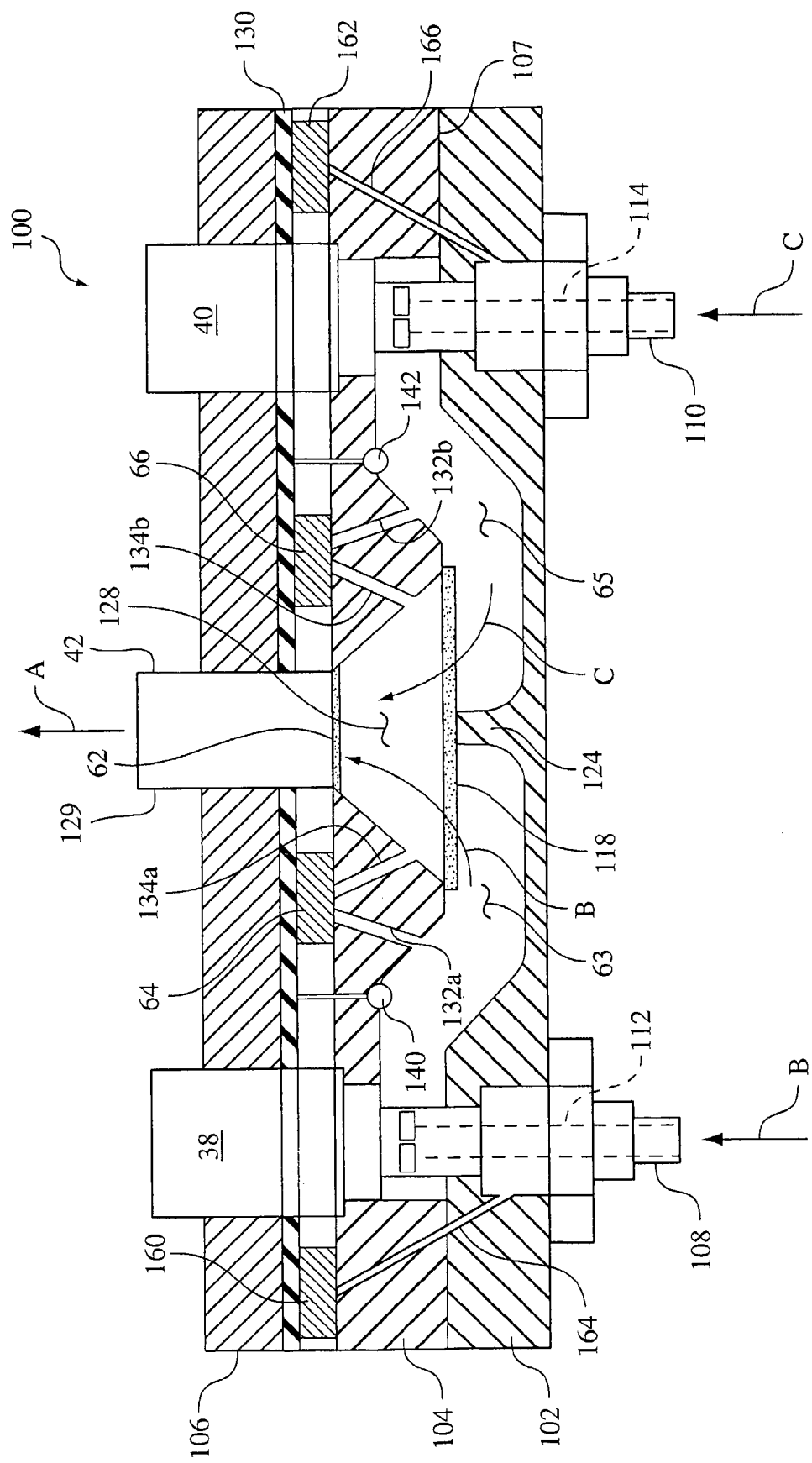
FIG. 9 is a cross-sectional view of the valve assembly of FIG. 7.

The present invention contemplates combining the components of valves 38 and 40, flow sensors 64 and 66, restrictor 62, and the associated conduits, in a pneumatic block 100, which is illustrated in FIGS. 7-9. In the illustrated exemplary embodiment, pneumatic block 100 includes three block elements 102, 104, and 106 that are constructed in a so-called "sandwich-technique". A gasket 107 is provided between block elements 102 and 104. Cavities are defined in block elements 102 and 104 to form gas flow paths 63 and 65 from valves 38 and 40 to restrictor 62, which is also defined by or housed in the pneumatic block. A first gas source, such as gas source 30, is coupled to a first inlet 108, and a second gas source, such as gas source 32, is coupled to a second inlet 110. A first path 112 in first inlet 108 communicates the gas to first valve 38, and a second path 114 in second inlet 110 communicates the gas to second valve 40.

The gas flow from valves 38 and 40 is communicated to a restrictor 118, which is defined by a pair of flow restriction nets or meshes 120 and 122. As discussed below, restrictor 118 provides a pressure drop along the gas flow path so that the flow of gas can be measured. In the illustrated embodiment, mesh 120 and 122 are sandwiched between a bridge member 124 and a cross-bar 126 provided in gasket 107. An advantage of restrictor 118 being in form of a large finely meshed net that is provided in one or more layers is that the volume occupied by the restrictor is kept to a minimum. The separate gas flow B and C flow through mesh 120 and 122 where they are mixed into gas flow A and output from the pneumatic block via an outlet port 129.

Although not shown in FIG. 9, pressure sensor 46 is operatively connected to gas flow path 42 in cavity 128, which is defined between valves 38, 40 and restrictor 62. Thus, cavity 128 corresponds to volume $V_B$ discussed above. As noted above, the present invention contemplates making cavity 128 larger or smaller depending on the desired amount of volume to be included in the control loop. As also noted above, the volume of cavity 128 can be made variable, for example, by providing a second chamber having a second volume that is selectively communicated to cavity 128 when it is desired to increase the volume of gas $V_B$ contained between the valves and the restrictor.

A circuit board 130 is also disposed in pneumatic block 100. Flow sensors 64 and 66, which are differential pressure sensors, are provided on circuit board 130. A connection terminal 132 is provided on circuit board to allow external communication with the controller 50. The ports of the pressure sensors are connected to the upstream side of restrictor 62 via conduits 132a and 132b, and to the downstream side of the restrictor via conduit 134a and 134b. Thus, restrictor 118 provides the pressure drop needed for flow sensing, and the signals output from the differential pressure sensors is a measurement of each gas flow. Despite the fact that the restrictor is a relatively large net, and large flows will cause a non-linearity in the output signal from the flow sensors. This non-linearity may be calibrated and compensated for in the electronics unit of the measurement system, i.e., by controller 50.

It should be understood that the present invention contemplates other configurations for restrictor 118. For example, one flow element can be provided in gas flow path 63 to provide the pressure drop between pressure pick-off points 132a and 134a and a separate flow element can be provided in gas flow path 65 to provide the pressure drop between pressure pick-off points 132b and 134b. These flow element can have any conventional configuration. For example, a narrow portion or taper can be provided in gas flow path 63 and/or 65 to provide this pressure drop.

The present invention further contemplates providing a first temperature sensor 140 in the flow channel between valve 38 and restrictor 118, and a second temperature sensor 142 between valve 40 and restrictor 118. Temperature sensors 140 and 142 measure the temperature of the gases that flow out of the valves 38 and 40. By means of this sensor signal, the gas volume may be compensated, so that it is put into relation with a desired temperature, e.g., of the ambient air, the patient's lung, or an arbitrary fixed temperature, e.g., 21° C. Temperature sensors 140 and 142 are any suitable temperature measuring device, as a thermistor, thermocouple, or an integrated silicon sensor.

As noted above, the present invention contemplates providing flow restrictor 62 downstream of cavity 128 and behind the point of measurement of pressure sensor 46. In the illustrated embodiment, restrictor 62 is achieved as a result of the tapering of the cross sectional area of the gas flow path from chamber 128 to outlet port 129. The present invention also contemplates that this flow restriction can be achieved by providing mesh, net, screen, or other flow restrictor in the gas flow path, either alone or in combination with the tapering of the cross-sectional area of the gas flow path. In addition, the second flow restriction enhances mixing of the first gas flow B and the second gas flow C.

As noted above, the outlet of each valve 38 and 40 has an associated flow meter 64 and 66, with the minimum volume connected thereto. This flow meter provides input signals to the flow regulator of each valve. The outlet of the valves is subsequently connected to a small, common chamber 128. A pressure sensor 46 is connected to this chamber, whose purpose is to provide a measurement point for the pressure in pressure control system having a relatively small volume. This embodiment provides a pneumatic block that has relatively short gas flow paths. As a result, small volumes are achieved in the pneumatic circuit even when two valves are used in combination, and, at the same time, a fast and stable control of the valves is achieved.

Pressure sensors 160 and 162 for monitoring the inlet pressures can also be provided on circuit board 130 and placed in fluid communication via conduits 164 and 166. These inlet pressures can be used to compensate the pressure/flow characteristics of valves 38 and 40 In other words, the flow of gas output from the valves is dependent on the inlet pressure. Pressure sensors 160 and 162 monitor this inlet pressure, which can then be used to maintain the proper output from the valves.

A technique for controlling the operation of electromagnetic valves 38 and 40 will now be described with reference to FIGS. 10A-10C. It should be noted that these figures illustrate a first embodiment of a schematic circuit diagram for controlling the operation of only one of the valves. Thus, the circuit shown in FIG. 10A for example, would be provided for each of valves 38 and 40.

In order to reduce the opening time of valves 38 and 40, the present invention contemplates driving these valves using a pulse-width-modulated voltage that is considerably higher than the rated voltage of the valve. In this manner, a desired current through the valves is produced rapidly. Hence, a high voltage quickly raises the current through the valve to a desired value. Thereafter, the voltage is pulse width modulated, so that the current follows a desired set-point value. During the time that the voltage pulse is off, a free-wheel diode is connected across the valve. This diode allows the stored energy to circulate, with the valve current through the valve during that time. In this manner, high power efficiency is achieved. When a quick shutting of a valve is needed, the energy stored in the electromagnet of the valve has to be removed. This may be done by connecting the free-wheel diode in series with a voltage source having a reversed polarity in relation to the regular voltage pulses. This driving configuration may likewise be pulse width modulated, such that a set-point of the current is followed.

A suitable circuit 170 for the above-described method is an H-bridge, which includes two active switches $S_A$ and $S_B$ and two diodes $D_A$ and $D_B$ connected across a power supply V and a capacitor C. FIGS. 10A-10C illustrate the various operating states for the circuit. Switches $S_A$ and $S_B$ operate under the control of controller 50.

Figure 10A:
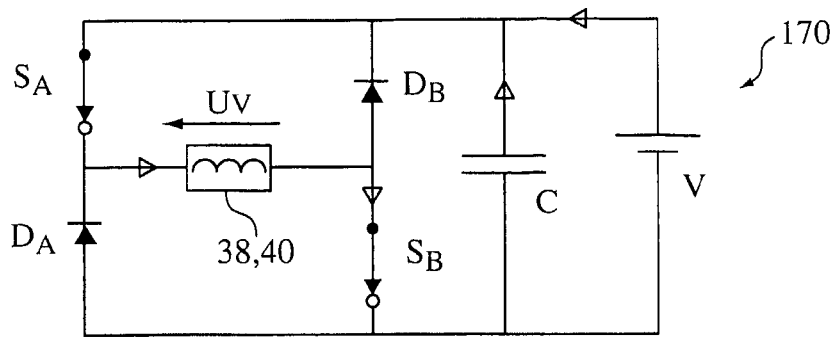
FIG. 10A-10C illustrate a first embodiment of a schematic circuit diagram for controlling the operation of the valve assembly using pulse modulation.
Figure 10B:
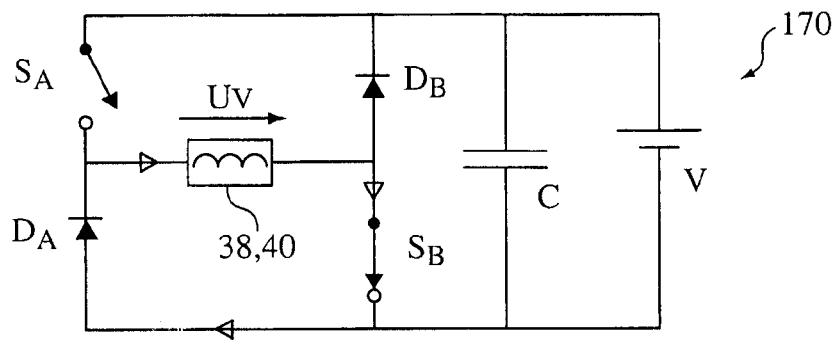
Figure 10C:
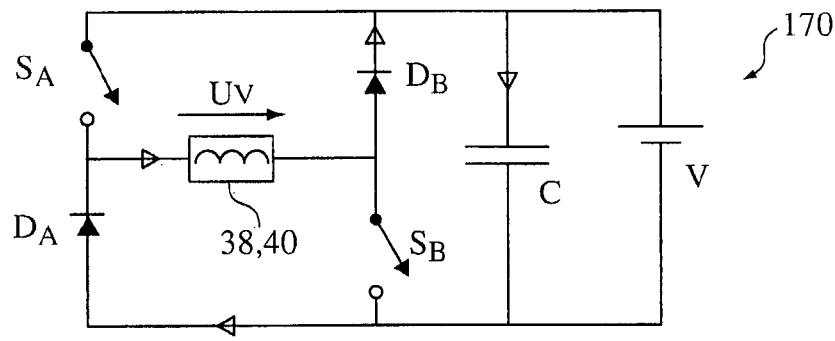

As shown in FIG. 10A, in order to open the valve as fast as possible, switches $S_A$ and $S_B$ are closed. As a result, current flows from capacitor C, as well as from power supply V through the valve. When the desired current through the valve is reached (which is measured, for example, via current measurement resistors), switch $S_A$ is opened and switch $S_B$ is maintained close. As a result, the valve current will circulate through diode $D_A$ and switch $S_B$, as shown in FIG. 10B. The voltage across the valve $U_V$ will then switch polarity and correspond to the diode voltage in the conducting diode $D_A$ along with resistive voltage drops in switch $S_B$. Thereafter, the desired current through the valve is controlled by pulse width modulating switch $S_A$. When the voltage pulses via $S_A$ are not being applied to the H-bridge, diode $D_A$ will work as a free-wheel diode.

If it is desired to close the valve rapidly, i.e., if too high of a current still flows through the valve, switch $S_B$ should also be opened. As shown in FIG. 10C, when switch $S_A$ and $S_B$ are opened, diodes $D_A$ and $D_B$ are placed in series with the reversed voltage $U_V$, corresponding to the supply voltage V. As a result, energy is removed from the valve much faster, and this energy is fed back into capacitor C and the power supply line.

Figure 11:
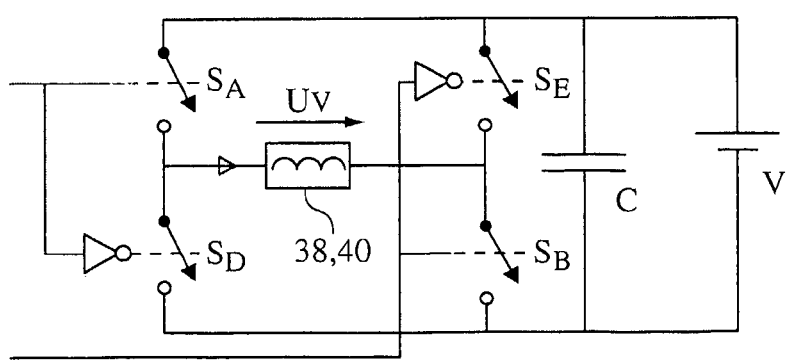
FIG. 11 illustrates a second embodiment of a schematic circuit diagrams for controlling the operation of the valve assembly using pulse modulation.

The present invention also contemplates that diodes $D_A$ and $D_B$ may be replaced by electrically controlled switches $S_D$ and $S_E$. This alternative embodiment is illustrated in FIG. 11. The control signals to these switches have in this case to be inverted in relation to the control of the switches in series in the H-bridge.

The principle of the invention is more advantageous because the energy of the actuating magnet is directly and harmonically transferred to the power supply capacitor C. Thus, the losses that appear (50%), in the case when a capacitor is discharged into another capacitor, are avoided, and furthermore the surge currents, which occur during such a discharge process, are avoided, which leads to an improved reliability, less interferences and above all a longer service life of the power supply capacitor.

The following table 1 summarize the different modes of the above-described control of the valves.

| Mode | $S_A$ | $D_A$ | $S_B$ | $D_B$ | C | FIG. |
|---|---|---|---|---|---|---|
| Fast opening | closed | currentless | closed | currentless | discharges | 10A |
| Control (pulse) | closed | currentless | closed | currentless | discharges | 10A |
| Control (free-wheel) | open | conducting | closed | currentless | unaffected | 10B |
| Rapid Shutting | open | conducting | open | conducting | charges | 10C |
| Shutting (free-wheel) | open | conducting | closed | currentless | unaffected | 10B |

While a valve is described above as being the means for controlling the pressure, flow, and/or volume of gas delivered to the user, it is to be understood that the present invention also contemplates controlling the pressure, flow, or volume of gas by controlling the operating speed of the pressure generator. This can be done alone or in combination with a valve. That is, in one embodiment, the operating speed of a compressor, such as the speed of a blower, alone is used to control the pressure of the patient and the valves are eliminated entirely. In another embodiment, pressure generator operating and one or more valves are used in combination to control the pressure of gas delivered to the patient.

It can be appreciated from the foregoing description and the accompanying figures that present invention provides a device for providing pressure control in the flow of gas delivered to a patient, that is capable of rapidly responding to changes in the system. This is made possible in an exemplary embodiment by providing valves operating as flow/pressure regulators and a flow restriction positioned between the valves and the outlet of the device. The volumes and dimensions of gas channels prior to the flow restriction are small with reference to the overall system, including the airway of the patient.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A ventilator adapted to deliver a flow of gas to an airway of a user, the ventilator comprising:
    a source of gas adapted to provide the flow of gas;
    a conduit that carries the flow of gas to the airway of a patient;
    a first valve operatively coupled to the conduit and adapted to control a pressure or rate of the flow of gas provided to the patient by the ventilator;
    a pressure sensor operatively coupled to the conduit between the valve and the patient and adapted to monitor a pressure of the gas in the conduit;
    a controller adapted to control the valve based on an output of the pressure sensor; and
    a restrictor provided in the conduit between the pressure sensor and the patient such that a first volume is defined in the conduit between the valve and the restrictor and a second volume is defined in the conduit between the patient and the restrictor, wherein the first volume is less than the second volume, and wherein the restrictor includes a plurality of flow restricting elements with a first one of the flow restricting elements having an increased cross sectional area as compared to a second one of the flow restricting, elements.

2. The ventilator of claim 1, wherein the first one of the flow restricting elements is coupled to the second one of the flow restricting elements by a wall that tapers a cross sectional area of the gas flow from the first one of the flow restricting elements to the second one of the flow restricting elements.

3. The ventilator of claim 1, wherein the pressure sensor is operatively connected to the gas flow between the first and second flow restricting elements.

4. The ventilator of claim 1, further comprising a flow sensor adapted to measure a rate of the flow of gas in the conduit, wherein the flow sensor is operatively coupled to the conduit between the valve and the restrictor.

5. The ventilator of claim 1, wherein the restrictor has a variable geometry.

6. The ventilator of claim 1, wherein the restrictor is configured to provide a non-linear pressure/flow relationship.

7. The ventilator of claim 1, wherein the restrictor has an adjustable degree of restriction, and wherein the controller controls the degree of restriction provided by the restrictor.

8. The ventilator of claim 1, further comprising a one-way check valve, placed downstream of the first volume.

9. The ventilator of claim 1, further comprising: a source of supplemental gas; a secondary conduit adapted to communicate the source of supplemental gas to the conduit; and a second valve operatively coupled to the secondary conduit to control a pressure or rate of the flow of the supplemental gas provided to the conduit.

10. The ventilator of claim 9, further comprising a fluid mixing element in the conduit downstream of a location where the second conduit is coupled to the conduit.

11. The ventilator of claim 9, wherein the first valve and the second valve are arranged on a common pneumatic block, and wherein the first conduit and the second conduit are defined in the pneumatic block.

12. The ventilator of claim 11, wherein the restrictor is disposed in the pneumatic block.

13. The ventilator of claim 1, wherein the first valve is actuated via an H-bridge circuit that comprises diagonally positioned reversed first and second diodes, diagonally positioned first and second switches, wherein the first valve is connected between central points of the H-bridge, wherein the H-bridge is connected to a power-supply voltage in which a first pole is coupled to top connection terminals of the H-bridge and a second pole is coupled to lower connection terminals of the H-bridge.

14. The ventilator of claim 13, further comprising a capacitor connected across the first and the second poles of the H-bridge.

15. The ventilator of claim 13, wherein the first and the second switches are actuated under the control of the controller such that (a) the valve is opened responsive to a first and the second switches being closed, (b) the valve is closed responsive to the first and the second switches being opened.

16. The ventilator of claim 13, wherein the position of the valve is controlled by closing one of the first and the second switches and pulse width modulating a remaining other of the first and the second switches.

17. A ventilator adapted to deliver a flow of gas to an airway of a user, the ventilator includes a source of gas adapted to provide the flow of gas, a conduit that carries the flow of gas to the airway of a patient, a first valve operatively coupled to the conduit and adapted to control a pressure or rate of the flow of gas provided to the patient by the ventilator, a pressure sensor operatively coupled to the conduit between the valve and the patient and adapted to monitor a pressure of the gas in the conduit, and a controller adapted to control the valve based on an output of the pressure sensor, characterized in that: a restrictor is provided in the conduit between the pressure sensor and the patient such that a first volume is defined in the conduit between the valve and the restrictor and a second volume is defined in the conduit between the patient and the restrictor, and wherein the first volume is less than the second volume, wherein the first valve is actuated via an H-bridge circuit that comprises diagonally positioned reversed first and second diodes, diagonally positioned first and second switches, wherein the first valve is connected between central points of the H-bridge, wherein the H-bridge is connected to a power-supply voltage in which a first pole is coupled to top connection terminals of the H-bridge and a second pole is coupled to lower connection terminals of the H-bridge.

18. The ventilator of claim 17, further comprising a capacitor connected across the first and the second poles of the H-bridge.

19. The ventilator of claim 17, wherein the first and the second switches are actuated under the control of the controller such that (a) the valve is opened responsive to a first and the second switches being closed, (b) the valve is closed responsive to the first and the second switches being opened.

20. The ventilator of claim 17, wherein the position of the valve is controlled by closing one of the first and the second switches and pulse width modulating a remaining other of the first and the second switches.

* * * * *